United States Patent [19]

Akiyama et al.

[11] Patent Number: 5,593,690

[45] Date of Patent: *Jan. 14, 1997

[54] SUSTAINED RELEASE PREPARATIONS

[75] Inventors: Yohko Akiyama, Ibaraki; Hidetoshi Horibe, Toyonaka; Minoru Yoshioka, Suita, all of Japan

[73] Assignee: Takeda Chemical Industries, Ltd., Osaka, Japan

[*] Notice: The term of this patent shall not extend beyond the expiration date of Pat. No. 5,399,357.

[21] Appl. No.: 388,520

[22] Filed: Feb. 14, 1995

Related U.S. Application Data

[62] Division of Ser. No. 807,630, Dec. 13, 1991, Pat. No. 5,399,357, which is a continuation of Ser. No. 433,223, Nov. 8, 1989.

[30] Foreign Application Priority Data

| Nov. 8, 1988 | [JP] | Japan | 63-282994 |
| Nov. 21, 1988 | [JP] | Japan | 63-294379 |
| Oct. 3, 1989 | [JP] | Japan | 1-259674 |

[51] Int. Cl.$^6$ ............... A61K 9/16; A61K 9/26; A61K 9/50; A61K 47/34

[52] U.S. Cl. ............... 424/457; 424/486; 424/458; 424/459; 424/461; 424/462; 424/470; 424/490; 424/494; 424/495; 424/497; 424/501; 514/785; 514/951; 514/963; 514/965

[58] Field of Search ............... 424/457, 486, 424/458–459, 461–462, 420, 490, 494–495, 497, 501; 514/785, 951, 963, 965

[56] References Cited

U.S. PATENT DOCUMENTS

| 3,857,933 | 12/1974 | Ross et al. | 424/20 |
| 4,751,241 | 6/1988 | Motoyama et al. | 514/532 |
| 4,777,050 | 10/1988 | Vadino et al. | 424/499 |
| 4,806,337 | 2/1989 | Swipes et al. | 424/408 |
| 4,844,907 | 7/1989 | Elger et al. | 434/499 |
| 4,857,336 | 8/1989 | Khawna et al. | 424/469 |

FOREIGN PATENT DOCUMENTS

| 208144 | 6/1986 | European Pat. Off. |
| 3224619 | 5/1983 | Germany |
| 58-13508 | 1/1983 | Japan |

OTHER PUBLICATIONS

M. R. Baichwal et al., "Sustained Release Capsules", The Indian Journal of Pharmacy, vol. 35, No. 5, Sep.–Oct. 1973, pp. 146–150.

Carstensen et al., "Physical and Chemical Properties of Calcium Phosphates for Solid State Pharmaceutical Formulations", Drug Development & Industrial Pharmacy, 16(7), pp. 1121–1133, 1990.

Patent Abstract of Japan, vol. 8, No. 145, Jul. 6, 1984.

*Primary Examiner*—Edward J. Webman
*Attorney, Agent, or Firm*—Foley & Lardner

[57] ABSTRACT

There is provided a matrix preparation produced by dispersing a pharmaceutically active ingredient into a matrix which is solid at ambient temperature and comprised of a fatty acid ester of a polyglycerol. The preparation has stable release-controlling ability, can be processed to fine granules, granules, capsules, tablets etc., and contributes to reduce the administration times of the active ingredient and side effects of the ingredient.

7 Claims, No Drawings

SUSTAINED RELEASE PREPARATIONS

This application is a division, of application Ser. No. 07/807,630, filed Dec. 13, 1991 (U.S. Pat. No. 5,399,357) which is a continuation of Ser. No. 07/433,223, filed Nov. 8, 1989, abandoned.

Present invention relates to stable, controlled release matrix preparations.

For the purposes of reducing a number of doses under sustaining the effect of a drug, and suppressing rapid elevation of drug concentration in blood to thereby alleviate side-effects or retaining drug concentration in blood for a long time, controlled release preparations, particularly sustained release pharmaceutical preparations have been studied with a variety of drug substances and by means of a number of methods. The controlled release preparations include, for example, capsule-type dosage forms comprising a drug-containing core portion covered with a membrane and matrix-type dosage forms consisting of a drug dispersed in the drug-release controlling layer.

These conventional controlled release preparations, which are required to be subjected to more sophisticated processing techniques, have been provided in the forms of tablets, capsules or granules.

Taking into consideration the fact that a recently increasing number of aged persons and children are given medicine, however, controlled release preparations in the form of fine granules are regarded desirable. In addition, one of the advantages that fine granules can offer lies in that their doses can be easily adjusted. However, stable controlled release preparations, particularly fine granules have not been obtainable, as far as they are produced in accordance with a production process for conventional controlled release preparations. Therefore, no controlled release fine granules has been commercialized so far in the past.

Under these circumstances, the present inventors conducted extensive investigation into controlled release matrix preparations which can be prepared by means of a practical and economical production method without the use of a solvent harmful to human beings, can also be easily adjusted in dissolution rate, is easy for patients to take and stable. As a result, present inventors found that when an active ingredient is dispersed into a matrix being solid at ambient temperature (15° to 35° C.) and consisting of or containing a fatty acid ester of a polyglycerol, which has not been employed in conventional matrix preparations, to produce a matrix preparation, particularly fine granules, an ideal controlled release matrix preparation can be obtained unexpectedly. The matrix preparation thus obtained excels remarkably in not only stability and release-controlling ability but also economy, toxicity, effect, etc. and furthermore that when an pharmaceutically active acidic ingredient and a solid base being insoluble or slightly soluble in water, or an active basic ingredient and an enteric substance, are dispersed during the production process for the matrix preparation as described above, there can be obtained a controlled release fine granules being provided with pH-independence, which allows an active ingredient to dissolve in the stomach and intestine at a constant rate. In addition to the above excellent characteristics, the resultant matrix preparations are suited for commercialization. The fine granules described here is named as Micromatrix system (MMS).

These findings have led the inventors to the completion of this invention.

Thus, this invention relates to:

1. A matrix preparation which comprises a pharmaceutically active ingredient dispersed into a matrix being solid at ambient temperature and consisting of a fatty acid ester of a polyglycerol or containing the same.

2. Fine granules or granules which comprise a pharmaceutically active ingredient dispersed into a matrix being solid at ambient temperature and consisting of a fatty acid ester of a polyglycerol or containing the same.

3. A matrix preparation according to the item 1, wherein microcrystalline wax is contained in the matrix.

4. Fine granules or granules according to the item 2, wherein microcrystalline wax is contained in the matrix.

5. Fine granules or granules according to the item 2 or 4, wherein the fine granules or granules are coated with a coating agent.

6. Capsules wherein the fine granules or granules according to the item 2 or 5 are filled.

7. Tablets which are produced by tableting the fine granules or granules according to the item 2 or 5.

8. Tablets according to the item 7, which contains a disintegrating agent.

9. Fine granules or granules which comprise a pharmaceutically active acidic ingredient and a water-insoluble or slightly water-soluble solid base dispersed into a matrix being solid at ambient temperature and consisting of a fatty acid ester of a polyglycerol or containing the same.

10. Fine granules or granules which comprise a pharmaceutically active basic ingredient and an enteric substance dispersed into a matrix being solid at ambient temperature and consisting of fatty acid ester of a polyglycerol or containing the same.

11. Fine granules or granules according to the item 9 or 10, which are coated with a coating agent.

12. Capsules wherein the fine granules or granules according to the item 9, 10 or 11 are filled.

13. Tablets which are produced by tableting the fine granules or granules according to the item 9, 10 or 11.

14. Tablets according to the item 13, wherein a disintegrating agent is contained.

The fatty acid ester of a polyglycerol in this invention is an ester formed by the combination of polyglycerol with a fatty acid. Polyglycerol is "a polyhydric alcohol having n (in a cyclic polyglycerin)–n+2 (in a straight or branched polyglycerin) hydroxyl groups and n–1 (in a straight or branched polyglycerin)–n (in a cyclic polyglycerin) ether combinations in one molecule" (Polyglycerin esters, p. 12, May 20, 1986, edited by Sakamoto Yakuhin Kogyo Co., Ltd., Japan). As the polyglycerol, there can be used, for example, those represented by the formula:

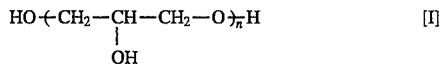

(wherein n is a degree of polymerization). Normally, n is an integer of 2 to 50, preferably 2 to 20 more preferably 2 to 10. As specific examples of such polyglycerols, there are used, for example, diglycerol, triglycerol, tetraglycerol, pentaglycerol, hexaglycerol, heptaglycerol, octaglycerol, nonaglycerol, decaglycerol, pentadecaglycerol, eicosaglycerol and triacontaglycerol, and among others, frequent use is made of tetraglycerol, hexaglycerol and decaglycerol. As the fatty acid, there can be used, for example, saturated or unsaturated higher fatty acids having a number of carbon atoms of 8 to 40, preferably 12 to 22. As the fatty acids, there are used, for example, palmitic acid, stearic acid, oleic acid, linolic acid, linoleic acid, myristic acid, lauric acid, ricinoleic acid, caprylic acid, capric acid and behenic acid, and among others, frequent use is made of stearic acid, oleic acid, lauric acid, ricinoleic acid, and the like. As the fatty acid esters of polyglycerols, there are used monoesters or polyesters from the polyglycerols and fatty acids as mentioned above. Such fatty acid esters of polyglycerols have ordinarily a molecular weight of 200 to 5000, preferably 300 to 2000, and an HLB (hydrophilic-lipophilic balance) of 1 to 22, preferably 1 to 15. Also, the fatty acid esters of polyglycerols can suitably be selected depending upon the type of active ingredients utilized, and there may be used, for example, those being capable of melting by warming active ingredients in proportions of 0.00001 to 5 g/ml, preferably 0.0001 to 1 g/ml. As specific examples of the fatty acid esters of polyglycerols, there may be used, for example, caprylyl di(tri)glyceride, capryl di(tri)glyceride, caprylyl mono(deca)glycerida, lauryl mono(deca)glyceride, lauryl mono(hexa)glyceride, lauryl mono(tetra)glyceride, oleyl di(tri)glyceride, oleyl di(tetra)glyceride, linolyl di(tri)glyceride, linolyl di(tetra)glyceride, linolyl di(hexa)glyceride, linolyl di(hepta)glyceride, stearyl mono(deca)glyceride, stearyl deca(deca)glyceride, stearyl mono(tetra)glyceride, stearyl mono(tetra)glyceride, stearyl mono(hexa)glyceride, stearyl sesqui(hexa)glyceride, oleyl sesqui(deca)glyceride, oleyl penta(hexa)glyceride, stearyl tri(hexa)glyceride, stearyl penta(hexa)glyceride, oleyl mono(hexa)glyceride, lauryl mono(deca)glyceride, stearyl tri(tetra)glyceride, stearyl penta(tetra)glyceride, oleyl mono(tetra)glyceride, oleyl penta(tetra)glyceride, lauryl mono(tetra)glyceride, palmityl mono(deca)glyceride, palmityl deca(deca)glyceride, palmityl mono(hexa)glyceride, palmityl sesqui(hexa)glyceride, palmityl tri(hexa)glyceride, palmityl penta(hexa)glyceride, palmityl mono(tetra)glyceride, palmityl tri(tetra)glyceride, palmityl penta(tetra)glyceride, and the like, either solely or in mixtures of more than two kinds thereof, and among others, frequent use is made for example of stearyl penta(tetra)glyceride (e.g., PS-310 produced by Sakamoto Yakuhin Co. of Japan), stearyl mono(tetra)glyceride (e.g., MS-310 produced by Sakamoto Yakuhin Co., Japan), stearyl penta(hexa)glyceride (e.g., PS-500 produced by Sakamoto Yakuhin Co., Japan) and stearyl sesqui(hexa)glyceride (e.g., SS-500 produced by Sakamoto Yakuhin Co. of Japan), stearyl mono(deca)glyceride, and the like. Particularly, in the case of the fatty acid ester of a polyglycerol is stearyl mono(deca) glyceride, excellent absorption of pharmaceutical active ingredient and stable controlled release ability are attained. These fatty acid esters of polyglycerols are used in such quantities as may correspond to about 0.001 to 50 times the weight of the active ingredient, preferably 0.005 to 5 times, however, the dose is not limited as far as the object of the invention is achieved.

In this invention matrixes containing fatty acid esters of polyglycerols are in the solid form at ambient temperature. The matrixes may best be incorporated with the fatty acid esters of polyglycerols as described above in such quantities as mentioned previously. As the matrix employable in this invention, there are used matrixes which are in the solid form at ambient temperature and have low melting points (30° to 150° C., preferably 40° to 120° C.). These matrixes can be incorporated, for example, with lipids in addition to the fatty acid esters of polyglycerols to thereby produce more preferred results. As these lipids, there are used pharmaceutically acceptable, water-insoluble lipids which demonstrate an action to regulate a dissolution rate of drugs, preferably lipids having a softening point or melting point of 40° to 120° C., preferably 40° to 90° C. As specific examples of these lipids, there are used for example hydrogenated oils (e.g., castor oil, cotton seed oil, soybean oil, rapeseed oil, beef tallow, and the like), beeswax, carnauba wax, spermaceti paraffin, lecitin, microcrystalline wax, fatty acids such as stearic acid and palmitic acid, or their salts (e.g., sodium salts, potassium salts, and the like), aliphatic alcohols such as stearyl alcohol and cetyl alcohol, and glycerides, among others. Frequent use is made for example of hardened cotton seed oil, hardened castor oil, hardened soybean oil, carnauba wax, stearic acid, stearyl alcohol and microcrystalline wax. The lipids may be used in an amount not hindering the object of the invention and normally they are used in such quantities as may correspond to about 0.01 to 100 times the weight of the active ingredient, preferably 1 to 20 times.

The matrixes being solid at ambient temperature usable in this invention can suitably be incorporated with additives being generally employable in the production of fine granules or granules, unless there is particular hindrance. For example, there can suitably be used excipients, such as lactose, corn starch, Avicel®, powdered sugar and magnesium stearate; binding agents, such as starch, sucrose, gelatin, powdered gum arabic, methylcellulose, sodium carboxymethylcellulose, hydroxypropylmethylcellulose and polyvinylpyrrolidone; disintegrating agents, such as calcium carboxymethylcellulose and substituted hydroxypropylcellulose; and other additives, such as coloring agents, flavoring agents, adsorbents, preservatives, wetting agents, antistatic agents and disintegration prolonging agents.

As the parmaceutically active ingredient, there may be employed drugs having relatively higher melting points (not lower than 121° C.), such as phenylpropanolamine hydrochloride, chlorphenylamine maleate, phenylepherin hydrochloride, theophylline, caffeine, procaineamide hydrochloride, sulfanylamide, cephalexin, ampicillin, molsidomine, indomethacin, sulfisoxazole, sulfadiazine, diazepam, valproic acid, quinidine sulfate, asprin and 3,4-dihydro-2,8-diisopropyl-3-thioxo-2H-1,4-benzoxadine-4-acetic acid (hereinafter referred to as "AD-5467"), delapril hydrochloride, ipriflavone, trepibutone and the like; drugs having relatively lower melting points (about 0° to 120° C., preferably e.g. 40° to 120° C.), such as isosorbide nitrate, ketoprofen, cyclanderate, idebenone and 2-(12-hydroxydodeca-5,10-dinyl)-3,5,6-trimethyl-1,4-benzoquinone (hereinafter referred to as "AA-861"), and peptides or proteins such as insulin, vasoopressin, interferon, IL-2, urokinase, a.FGF (acidic fibroblast growth factor), b.FGF (basic fibroblast growth factor), etc. The matrix preparation of present invention can permit these drugs to gradually dissolve or/and be absorbed in the digestive tracts.

The solubilty and absorption from gastrointestinal tract of active ingrectients vary with physicochemical properties. Generally speaking, base active ingredients, which show an increased solubility in the acid pH range but a decreased solubility in the alkali pH range, dissolve rapidly in the stomach that they pass through under the influence of acid gastric juice, but dissolve slowly in the neutral to weakly alkaline intestine. On the other hand, acid active ingredients, which exhibit an enhanced solubility in the alkaline pH region but a lower solubility in the acid pH region, dissolve rapidly in the neutral to weakly alkaline intestine but dissolve slowly in the stomach that they pass through under the influence of acid gastric juice. Accordingly, in order to retain the appropriate release-controlled dissolution of the active ingredient in the pH-independent manner so that its dissolution may be realized at a constant rate in both the stomach and intestine, in this invention, the acid active ingredient and water-insoluble or slightly water-soluble solid base, or the base active ingredient and enteric substance, are dispersed into the matrix of the fatty acid ester of a polyglycerol or the matrix containing the same which is in the solid form at ambient temperature.

The acid active ingredient as mentioned herein is that of which aqueous solutions present acidity (e.g. pH of not less than 1.5 but less than 7.0, preferably 2.0 to 6.8), or that which has acid group(s) (e.g. carboxyl group etc.). As the ingredient, there may be used, for example, indomethacin, salicylic acid, AD-5467, trepibutone, aspirin, valproic acid, ketoprofen, ibuprofen, epinephrine, haloperidol, reserpine, ascorbic acid, acetaminophen and probenecide and AD-5467; trepiptone, indomethacin, and the like are among others preferably used. The solid base used includes water-insoluble or slightly water-soluble (solubility in water at 37° C. of not more than 0.1 g/ml, preferably not more than 0.001 g/ml) solid bases, whereupon the less soluble ones can produce more desirable results. As these solid bases, there are used oxides, hydroxides, inorganic acid salts or organic acid salts of metals of Groups I, II and III in the periodic table, either solely or in mixtures of not less than two kinds thereof, such as magnesium oxide, magnesium hydroxide, magnesium silicate, magnesium carbonate, aluminum silicate, aluminum hydroxide, silicic acid (cyloid, aerosol), magnesium aluminometasilicate (neusiline), magnesium stearate, aluminum stearate and sodium stearate. The solid bases have normally a particle size of not more than 50 μm, preferably 0.05 to 20 μm, while they are used in the proportions of usually 1 to 80 weight %, preferably 1 to 50 weight %, more preferably 10 to 30 weight %, to the total amount.

The basic active ingredient is that of which aqueous solutions present alkalinity (pH 7.0 to 13.0, preferably 7.0 to 10.5), or that which has basic group(s) (e.g. amino group etc.). As the ingredient, there are used, for example, vinpocetine, estazolam, acetazolamide, papaverine, tolbutamide, acetohexamide, theophylline, verapamil, quinidine, propranolol, morphine, ephedrine, scopolamine, chlorpromazine, manidipin hydrochloride, and the like with vinpocetine, acetazolamide, etc. being among others frequently used. As the enteric substance, there are used substances which hardly dissolve in the stomach but start to dissolve in the intestine, whereby finely powdered (10 to 0.05 μm) substances as used can particularly produce desired results. Such enteric substances may be acidic compounds of high-molecular (molecular weights ranging from 30,000 to 500,000, preferably from 70,000 to 400,000), and there are used, for example, hydroxypropylmethylcellulose phthalate, cellulose acetate phthalate, carboxymethylethylcellulose (CMEC AQ®; produced by Kojin Co., Japan), methacrylic acid/methyl methacrylate copolymers (Eudragit® L100-55, Eudragit L-100, Eudragit S-100; produced by Rohm Pharma Co., West Germany) and the like, either solely or in mixtures of not less than two kinds of these acidic high molecular weight compounds. Particularly, Eudragit L100-55, etc. are frequently used. The enteric substances normally show a particle size of not more than 50 μm, preferably 0.05 to 10 μm, while they are used in proportions of usually 1 to 80 weight %, preferably 1 to 50 weight %, more preferably 10 to 30 weight %, to the total weight.

The active ingredients inclusive of the above-mentioned acid and basic active ingredients are contained in the matrix preparation of this invention in the proportions of 0.005 to 75 weight %, preferably 0.01 to 50 weight %, to the total weight of the fine granules.

The matrix preparation of this invention can be produced by dispersing (the term "disperse" includes the dispersion of not only solid but also liquid substances) an active ingredient into a matrix of a fatty acid ester of a polyglycerol or a matrix containing the same which is in the solid form at ambient temperature, followed by bringing to fine granules or granules; dispersing an acid active ingredient and a water-insoluble or slightly water-soluble solid base into a matrix of a fatty acid ester of a polyglycerol or a matrix containing the same which is in the solid-form at ambient temperature, followed by bringing to fine granules or granules; or dispersing a basic active ingredient and an enteric substance into a matrix of a fatty acid ester of a polyglycerol or a matrix containing the same which is in the solid form at ambient temperature, followed by bringing to fine granules or granules. Thus, the stable, controlled release matrix preparations, particularly fine granules or granules of present invention can be obtained for example by melting by warming (40° to 150° C. preferably 50° to 110° C.) a fatty acid ester of a polyglycerol alone or in conjunction with the above-mentioned additives being capable of forming with it a matrix being solid at ambient temperature, adding to the melted substance an active ingredient, an acid active ingredient and a water-insoluble or slightly water-soluble solid base or a basic active ingredient and an enteric substance in suitable amounts to produce a dispersion, followed by cooling and bringing to a matrix, particularly fine granules or granules. On the occasion when the fatty acid ester of a polyglycerol is melted by warming, the above-described lipid and additives may be melted by warming together with it or may be melted individually and then mixed with it. In addition, the active ingredient as well as particles of the additives can be added simultaneously. A known granulator can be employed to produce the objective matrix, such as fine granules (normally composed of not less than 75 weight % of particles of 500 to 10 μm, not more than 5 weight % of particles of not less than 500 μm and not more than 10 weight % of particles of not more than 10 μm; particularly not less than 75 weight % of particles of 500 to 105 μm, not more than 5 weight % of particles of not less than 500 μm and not more than 10 weight % of particles of not more than 74 μm), granules (composed of, for example, not less than 90 weight % of particles of 1410 to 500 μm and not more than 5 weight % of particles of not more than 177 μm) and the like.

Granulation under cooling is particularly preferred for producing fine granules, and for example, it is desirable to produce spherical fine granules through spray cooling, in particular through spray-chilling. Spray chilling can be performed for example by dripping or adding dropwise the melted material at a constant rate (2 to 200 g/min., preferably 5 to 100 g/min.) onto a high-speed rotating disc (e.g., a smooth or flat disc, such as a disc made of aluminum, having 5 to 100 cm in diameter, preferably 10 to 20 cm) at a rotation number of usually 10 to 6,000 rpm, preferably 900 to 6,000 rpm, more preferably 1,000 to 3,000 rpm.

Present matrix preparations, particularly fine granules or granules may be those coated with a coating agent by a per se known method for reforming their surfaces, masking their taste or giving them a solubility in the intestine etc. As the coating agent, there are used, for example, hydroxypropylmethylcellulose, ethylcellulose, hydroxymethylcellulose, hydroxypropylcellulose, sugar powder, polyoxyethylene glycol, Tween 80, Pluronic F 68, castor oil, cellulose acetate phthalate, hydroxypropylmethylcellulose acetate succinate, acrylic acid polymer (e.g. Eudragit® L100-55, L-100, S-100, produced by Rohm Pharma co., West Germany), carboxymethylcellulose, polyvinylacetyl, diethylaminoacetate, waxes, and the like, as well as pigments, such as talc, titanium oxide, red etc. These agents may be used solely or in combination with two kinds or more to make one or two layers of coating. For the coating, there can be employed per se known method. Namely, the coating may be carried out by, for example, spraying a liquid made by dispersing or dissolving the coating agent in water or an organic solvent on a matrix by pan-coating, fluidized-coating or centrifugal fluidized coating.

The coating of fine granules is preferably carried out at a temperature of 25° to 70° C., preferably 25° to 40° C.

The controlled release matrix preparations preferably take the form of fine granules or granules but in cases where persons involved in the medical service or patients ask for tablets for the purpose of convenience, the matrix, preferably the fine granules or granules as obtained by the above procedure can be compressed to tablets, together with excipients (among others, disintegrating agent, etc. as mentioned above) added, if necessary, in accordance with the conventional method at a pressure of, for example, 0.2 to 2.0 ton/cm$^2$, preferably 0.2 to 1.0 ton/cm$^2$. Furthermore, the fine granules or granules can be filled into capsules by a conventional manner to process to capsule preparations. These tablets or capsules have excellent effects and stable release rate equal to the present matrix preparations, particularly fine granules or granules; however, it is to be understood that such tablets and capsules are included in the scope of present invention.

The present matrix preparations of fine granules, granules, tablets, capsules etc. obtained by the above procedures can be put into use in the same manner as the conventional fine granules, granules, tablets, capsules, and the like, for example, by administering them orally to subjects (mammals, such as human beings, domestic animals and experimental animals) to whom the active ingredient is intended for used.

The present matrix preparations of fine granules, granules, tablets and capsules possess the extremely stable controlled release ability being free from variation in drug (active ingredient) release rate and hardly show any change in the drug release pattern even after storage for a prolonged period of time, and further a bad taste or odor of a drug can be masked in the preparation. Moreover, the present preparations are easy to control the drug release rate, are applicable to a wide range of drugs, do not require the use of organic solvent in the production process, do not cause air pollution in the production steps, do not provide any risk of solvent remaining in the pharmaceutical preparations nor produce any static electric charge and can be produced by the simplified production process requiring no special equipment, and consequently can be said to be the ideal controlled release preparations.

Described in the following are the examples to illustrate this invention in more particularly, but this invention is understood to not be limited to such examples.

In the following examples, the dissolution rate was determined by the method referred below:

According to Method 2 (paddle method) of "The Method for Determining Dissolution" in Japanese Pharmacopoeia, 11th Edition (herein after referred as "J.P. 11 Ed."), the dissolution from a test material was carried in 900 ml of dissolution medium containing a surfactant under 100 rpm of revolution; sampling of the medium was carried periodically, and the dissolution rates were calculated on the UV-absorbance of each filtrate of the samples.

EXAMPLE 1

A 80 g quantity of stearyl penta(tetra)glyceride (PS-310® produced by Sakamoto Yakuhin Co., Japan; hereinafter referred to as PS-310) was warmed and melted at 90° C., and 20 g of theophylline was put into the molten material, followed by stirring for 30 minutes to achieve dispersion. The dispersion was warmed at 90° C. and dripped at a rate of 20 g/min. onto an aluminum-made disc of 15 cm in diameter revolving at 2000 rpm. to produce spherical fine granules which passed through a 42 mesh sieve but did not pass through a 60 mesh sieve (hereinafter described briefly as "42/60 mesh").

EXAMPLE 2

By following the same procedure as described in Example 1 (namely through spray chilling), except that 37.5 g of stearyl mono(tetra)glyceride (MS-310® produced by Sakamoto Yakuhin Co., Japan; hereinafter referred to as MS-310) and 42.5 g of hydrogenated cotton seed oil were warmed and melted at 90° C. and 20 g of theophylline was put into the molten material, followed by stirring for 30 minutes to allow dispersion. There were obtained 42/60 mesh spherical fine granules.

EXAMPLE 3

By conducting spray chilling in the same manner as described in Example 2 while using:

25 g of MS-310

55 g of hydrogenated cotton seed oil 20 g of theophylline, there were obtained 42/60 mesh spherical fine granules.

EXAMPLE 4

By carrying out spray chilling in the same manner as described in Example 2 while using:

125 g of MS-310

67.5 g of hydrogenated cotton seed oil 20 g of theophylline, there were obtained 42/60 mesh spherical fine granules.

EXAMPLE 5

By conducting spray chilling in the same manner as described in Example 2 while using:

20 g of MS-310

40 g of hydrogenated cotton seed oil 40 g of 3,4-dihydro-2,8-diisopropyl-3-thioxo-2H-1,4-benzoxazine-4-acetic acid, there were obtained 32/42 mesh spherical fine granules.

EXAMPLE 6

By conducting spray chilling in the same manner as described in Example 2 while using:

1 g of MS-310

109 g of hydrogenated cotton seed oil 90 g of theophylline, there were obtained 42/60 mesh spherical fine granules.

EXAMPLE 7

By carrying out spray chilling in the same manner as described in Example 1, except that 1 g of MS-310, 45 g of lactose and 110 g of hydrogenated cotton seed oil were warmed and melted at 90° C. and 45 g of theophylline was put into the molten material, followed by stirring for 30 minutes to allow dispersion, there were obtained 42/60 mesh spherical fine granules.

EXAMPLE 8

By conducting spray chilling in the same manner as described in Example 2 while using:
  1 g of MS-310
  100 g of stearyl alcohol
  100 g of 3,4-dihydro-2,8-diisopropyl-3-thioxo-2H-1,4-benzoxazine-4-acetic acid,
there were obtained 48/60 mesh spherical fine granules.

EXAMPLE 9

Mixed were 200 g of the fine granules as obtained in Example 8, 75 g of Avicel®, 25 g of ECG 505® (a disintegrating agent produced by Nichirin Chemical Co. of Japan) and 0.9 g of magnesium stearate, and the mixture was compressed into tablets at a pressure of 0.2 ton/cm$^2$ with the use of a punch of 11 mm in diameter (radius of curvature of 15 R).

EXAMPLE 10

By conducting spray chilling in the same manner as described in Example 1 after warming and melting 5 g of MS310 and 20 g of hydrogenated cotton seed oil at 90° C., charging 1 g of vinpocetine and 15 g of Eudragit L100-55 into the molten material and stirring the mixture for 30 minutes to allow dispersion, there were obtained 42/60 mesh spherical fine granules.

EXAMPLE 11

By following the same procedure as described in Example 10 while using 3 g of MS-310, 20 g of hydrogenated cotton seed oil, 1 g of vinpocetine and Eudragit L100-55, there were obtained 42/60 mesh spherical fine granules.

EXAMPLE 12

By conducting spray chilling in the same manner as described in Example 1 after warming and melting 7 g of MS310 and 21 g of hydrogenated cotton seed oil at 90° C., charging 5 g of AD-5467 and 10 g of magnesium hydroxide and stirring the mixture for 30 minutes, there were obtained 42/60 mesh spherical fine granules.

EXAMPLE 13

By following the same procedure as described in Example 12 except that 10 g of synthetic aluminum silicate in place of 10 g of magnesium hydroxide, there were obtained 42/60 mesh spherical fine granules.

EXAMPLE 14

PS-310 (91 g) was melted by heating (90° C.), idebenone (9 g) was thrown thereinto, and the mixture was melted by stirring for 30 minutes maintaining the mixture at 90° C. By the same procedure as Example 1, 60/80 mesh of fine granules were obtained.

As a comparative experiment, hardened cotton seed oil (91 g) and idebenone (9 g) were processed in the same manner as above to obtain 42/62 mesh of fine granules.

The dissolution (%; hereinafter this means weight % unless specifically defined) of the drug from these fine granules stored at 40° C. are shown in Table 1.

TABLE 1

| | | Dissolution (%) Hour | | | | | |
|---|---|---|---|---|---|---|---|
| | | 1 | 2 | 3 | 4 | 5 | 6 |
| Fine granules made by using PS-310 | Immediately after production | 55.7 | 74.2 | 85.7 | 93.9 | 99.3 | 102.6 |
| | After 1 month at 40° C. | 60.8 | 73.3 | 82.2 | 88.6 | 92.9 | 96.5 |
| | After 2 months at 40° C. | 61.4 | 74.1 | 82.8 | 89.2 | 94.1 | 97.2 |
| Fine granules made by using hardened cotton seed oil | Immediately after production | 27.3 | 36.0 | 43.2 | 49.4 | 54.9 | 59.9 |
| | After 1 month at 40° C. | 33.0 | 44.0 | 53.0 | 61.0 | 68.0 | 74.0 |

From Table 1, the following facts are clarified:

The dissolution rate of idebenone from the fine granules obtained by using hardened cotton seed oil after 1 month storage at 40° C. is increased as compared with those of immediately after the production. To the contrary, the dissolution rate from the present fine granules using PS-310 shows a little change after 1 month storage and no change after 4 months storage; therefore, the release-sustaining ability of present fine granules is stable.

EXAMPLE 15

PS-310 (75 g) and MS-310 (5 g) were melted together by heating at 90° C., and then trepibutone (10 g) and magnesium oxide (30 g) were thrown thereinto and dispersed for 30 minutes maintaining the mixture at 80° C., followed by treating in the same manner as Example 1 to obtain 42/60 mesh of spherical fine granules.

The dissolution rates of the product in the mediums of I, II and pH 5 as described in J.P. 11 Ed. are shown in Table 2.

TABLE 2

| | Dissolution (%) Hour | | | | | |
|---|---|---|---|---|---|---|
| | 1 | 2 | 3 | 4 | 5 | 6 |
| Medium I (pH 1.2) | 19.4 | 29.4 | 37.1 | 43.8 | 50.0 | 54.7 |
| pH 5.0 | 28.7 | 36.3 | 45.6 | 55.1 | 63.8 | 70.1 |
| Medium II (pH 6.8) | 29.5 | 37.6 | 45.5 | 52.9 | 60.7 | 66.8 |

From Table 2, it is apparent that the present fine granules exhibit almost the same rate of drug release in a wide range of pH; therefore the fine granules have stable controlled release ability.

The dissolution rates of fine granules obtained in Example 15 in medium I and II after storage for 4 months at 40° C. are shown in Table 3.

TABLE 3

| | \multicolumn{6}{c}{Hour} |
|---|---|---|---|---|---|---|
| | 1 | 2 | 3 | 4 | 5 | 6 |
| Dissolution (%) in Medium I | | | | | | |
| Immediately after production | 19.4 | 29.4 | 37.1 | 43.8 | 50.0 | 54.7 |
| After 4 months at 40° C. | 18.9 | 30.0 | 38.1 | 44.2 | 49.2 | 53.7 |
| Dissolution (%) in Medium II | | | | | | |
| Immediately after production | 29.5 | 37.6 | 45.5 | 52.9 | 60.7 | 66.8 |
| After 4 months at 40° C. | 28.9 | 37.1 | 45.1 | 53.2 | 60.5 | 66.4 |

From Table 3, it is apparent that the release controlling ability of the present fine granules is extremely stable, because the dissolution rates after 4 months storage unchange as compared with those of immediately after the production.

EXAMPLE 16

PS-310 (75.2 g) and MS-310 (20.8 g) were melted together and 4 g vinpocetine and Eudragit® L100-55 (Rohm Pharma. Co., West Germany) (60 g) were put thereinto and dispersed by stirring for 30 minutes maintaining the mixture at 80° C., followed by treating in the same manner as Example 1 to obtain 42/60 mesh of spherical fine granules.

The dissolution rate of the product in mediums I and II after storage for 2 weeks and 4 months are shown in Table 4.

TABLE 4

| | \multicolumn{6}{c}{Dissolution (%)} |
|---|---|---|---|---|---|---|
| | \multicolumn{6}{c}{Hour} |
| | 1 | 2 | 3 | 4 | 5 | 6 |
| Medium I (pH 1.2) | 43.4 | 63.2 | 75.1 | 83.5 | 89.8 | 95.1 |
| Medium II (pH 6.8) | 48.9 | 64.7 | 71.5 | 75.4 | 79.1 | 83.6 |

From Table 4, it is apparent that the present fine granules are those exhibiting stable release controlling ability, because they release a drug in almost the same rate under conditions having varied pHs.

EXAMPLE 17

PS-310 (75 g) and MS-310 (21 g) were melted together by heating at 90° C., and vinpocetine (4 g) and Euragit® L100-55 (produced by Rohm Pharma. Co., West Germany) (60 g) were put thereinto and dispersed by stirring for 30 minutes maintaining the mixture at 80° C., followed by treating in the same manner as Example 1 to obtain 42/60 mesh of spherical fine granules. The dissolution rates of the product in mediums I and II after storage of 2 weeks and 4 months at 40° C. are shown in Table 5.

TABLE 5

| | \multicolumn{6}{c}{Hour} |
|---|---|---|---|---|---|---|
| | 1 | 2 | 3 | 4 | 5 | 6 |
| Dissolution (%) in Medium I | | | | | | |
| Immediately after production | 36.5 | 56.4 | 69.0 | 77.5 | 84.4 | 89.8 |
| After 2 weeks at 40° C. | 41.6 | 61.4 | 73.1 | 81.5 | 87.9 | 92.6 |
| After 4 months at 40° C. | 52.5 | 66.5 | 81.0 | 87.0 | 91.6 | 96.4 |
| Dissolution (%) in Medium II | | | | | | |
| Immediately after production | 57.7 | 73.8 | 79.3 | 82.5 | 85.9 | 88.5 |
| After 2 weeks at 40° C. | 55.6 | 69.3 | 75.1 | 79.8 | 83.6 | 87.1 |
| After 4 months at 40° C. | 58.7 | 72.1 | 84.4 | 87.4 | 92.0 | 92.3 |

From Table 5, it is apparent that the present fine granules are those exhibiting stable release-controlling ability which is unchanged after two weeks in comparison to immediately after the production, and that the stability is unchanged after 4 months at 40° C.

EXAMPLE 18

PS-310 (75 g) and MS-310 (25 g) were melted together by heating at 90° C., and then AD-5467 (100 g) was put thereinto and dispersed by stirring for 30 minutes maintaining the mixture at 90° C., followed by treating in the same manner as Example 1 to obtain 42/80 mesh of fine granules.

EXAMPLE 19

PS-310 (52 g) and MS-310 (4 g) were melted together by heating at 90° C., and AD-5467 (10 g) and magnesium hydroxide (40 g) were put thereinto and dispersed by stirring for 30 minutes maintaining the mixture at 90° C., followed by treating in the same manner as Example 1 to obtain 42/60 mesh of spherical fine granules. The dissolution rates of the product after storage at 40° C. are shown in Table 6.

TABLE 6

| | | \multicolumn{6}{c}{Dissolution (%)} |
|---|---|---|---|---|---|---|---|
| | | \multicolumn{6}{c}{Hour} |
| | | 1 | 2 | 3 | 4 | 5 | 6 |
| Medium I | Immediately after production | 54.1 | 69.8 | 77.6 | 91.1 | 96.7 | 99.5 |
| | After 1 month at 40° C. | 48.1 | 60.1 | 76.1 | 88.1 | 96.3 | 99.3 |
| Medium II | Immediately after production | 46.5 | 65.6 | 77.0 | 83.2 | 86.9 | 88.2 |
| | After 1 month at 40° C. | 47.3 | 70.5 | 80.7 | 86.1 | 86.4 | 86.4 |

From Table 6, it is apparent that the present fine granules are those exhibiting stable release-controlling ability which is unchanged after 1 month in comparison to those of immediately after the production.

EXAMPLE 20

PS-310 (192 g) and MS-310 (32 g) were melted together by heating at 90° C., and then AD-5467 (40 g) and magnesium hydroxide (160 g) were thrown thereinto and dispersed by stirring for 30 minutes maintaining the mixture at 90° C., followed by treating in the same manner as Example 1 to obtain 42/60 mesh of spherical fine granules.

| | |
|---|---|
| AD-5467 | 40 g |
| PS-310 | 216 g |
| MS-310 | 8 g |
| Magnesium hydroxide | 160 g |

The above materials were treated in the same manner as Example 20 to obtain 60/80 mesh spherical fine granules.

The dissolution rates of the products obtained in Examples 20 and 21 in mediums I and II are shown in Table 7.

TABLE 7

| | | Dissolution (%) | | | | | |
|---|---|---|---|---|---|---|---|
| | | Hour | | | | | |
| | | 1 | 2 | 3 | 4 | 5 | 6 |
| Example 20 | Medium I | 66.5 | 89.3 | 97.5 | 100.0 | 100.0 | 100.0 |
| | Medium II | 76.7 | 88.5 | 90.5 | 90.3 | 90.6 | 90.8 |
| Example 21 | Medium I | 36.6 | 50.0 | 58.8 | 65.9 | 71.7 | 76.3 |
| | Medium II | 36.8 | 48.4 | 71.8 | 78.5 | 81.8 | 82.5 |

As seen from Table 7, the present fine granules release AD-5467 at almost constant rate even under conditions having varied pHs, and granules having fast dissolution rate (Example 20) or slow dissolution rate (Example 21) independent of pH can be produced by changing the ratio of fatty acid ester of polyglycerol in present matrixes.

Fine granule preparations containing AD-5467 obtained in Examples 20 and 21, and 4 mg/ml solution of AD-5467 in aqueous 5 W/V % suspension of gum arabic as a contrast were administered to each group of four rats (SD-rat, 8 weeks aged, male), respectively.

Each material was administered to fasted animals in a dose of 10 mg/Kg (body weight) of AD-5467 and concentrations in the blood were determined (Table 8).

TABLE 8

| | Concentration in blood (μg/ml) | | | | | | |
|---|---|---|---|---|---|---|---|
| | Hour | | | | | | |
| | 0.25 | 0.5 | 1 | 1.5 | 2 | 3 | 5 | 7 |
| Example 20 | 0.75 | 2.30 | 3.14 | 2.22 | 1.19 | 0.52 | 0.53 | 0.23 |
| Example 21 | 0.16 | 0.73 | 0.88 | 1.12 | 1.23 | 0.79 | 0.57 | 0.69 |
| Suspension in 5 w/v % aqueous gum arabic | 5.97 | 2.85 | 1.38 | 0.70 | 0.41 | 0.20 | 0.20 | 0.13 |

Table 8 shows the following facts;

In the case of administering the aqueous suspension of gum arabic containing AD-5467, the concentration of AD-5467 in the blood reachs to the peak at 15 minutes and thereafter falls rapidly. To the contrary, present fine granules of Example 20 or 21 exhibits the peak after 1 hour or 2 hours, respectively. Therefore, present fine granules have excellent release-controlling ability.

EXAMPLE 22

Stearyl mono(deca)glyceride (produced by Sakamoto Yakuhin Co.) (92 g) was melted by heating at 90° C., and ipriflavone (18 g) was put thereinto and dispersed by stirring for 30 minutes maintaining the mixture at 90° C., followed by treating in the same manner as Example 1 to obtain 42/60 mesh of spherical fine granules.

The fine granules were administered orally to four beagles (aged 1 year, about 10 Kg) each in a dose of containing 200 mg of ipriflavone, and the concentration of 7-hydroxy-3-phenyl-4H-1-benzopyran-4-one (main metabolite of ipriflavone) in the blood was determined. The results are shown in Table 9. As the contrast, the dispersion of 200 mg of ipriflavone in 5 W/V % aqueous gum arabic suspension (hereinafter abbreviated as "suspension") was employed.

TABLE 9

| | Concentration in blood (μg/ml) | | | | | | |
|---|---|---|---|---|---|---|---|
| | Hour | | | | | | |
| | 0.25 | 0.5 | 1 | 1.5 | 2 | 3 | 5 | 7 |
| Example 22 | 43.1 | 120.7 | 198 | 187.1 | 209.2 | 219.5 | 125.7 | 121.7 |
| Suspension | 0.1 | 7.2 | 10.3 | 21.9 | 33.0 | 25.0 | 32.1 | 25.6 |

As seen from Table 9, the absorption of ipriflavone from present fine granules obtained in Example 22 amounts to 10 times higher and sustains longer as compared with "suspension".

EXAMPLE 23

(1) PS-310 (860 g) and MS-310 (100 g) were melted together by heating at 90° C., and 90 g of phenylpropanolamine was thrown thereinto and dispersed by stirring for 30 minutes maintaining the mixture at 90° C., followed by treating in the same manner as Example 1 to obtain 30/42 mesh of spherical fine granules.

(2) The fine granules (300 g) obtained in the above (1) were loaded into a fluid-bed drier (FD-3S; Fuji Sangyo Co., Japan) and sprayed with 5 W/V % aqueous solution of hydroxypropylmethylcellulose (TC-5R; Shinetsu Chemical Co., Japan), controlling the temperature of inlet air at 45° C. and that of granules at 35° C.; thereby coated fine granules were obtained.

The dissolution rates of phenylpropanolamine in water from the fine granules obtained in Example 23 (1) and (2) are shown in Table 10.

TABLE 10

| | Dissolution | | | |
|---|---|---|---|---|
| | Hour | | | |
| | 1 | 2 | 3 | 4 |
| Example 23(1); fine granules | 22.9 | 31.3 | 37.8 | 38.6 |
| Example 23(2); coated fine granules | 18.8 | 27.0 | 33.5 | 34.9 |

As seen from Table 10, present fine granules exhibit almost unchanged elution rate after and before coating and have stable release-controlling ability.

EXAMPLE 24

(1) PS-310 (800 g) and MS-310 (100 g) were melted together by heating at 90° C., and then caffeine (100 g) was thrown thereinto and dispersed by stirring for 30 minutes maintaining the mixture at 90° C., followed by treating in the same manner as Example 1 to obtain 42/60 mesh of spherical fine granules.

(2) The fine granules (250 g) obtained in the above (1) were loaded into a fluid-bed drier (FD-3S; Fuji Sangyo Co., Japan) and sprayed with 5 W/V % solution of hydroxypropylmethylcellulose in ethanol, controlling the inhalant air at 45° C. and the granules at 35° C.; thereby coated fine granules were obtained.

EXAMPLE 25

The fine granules (100 g) obtained in Example 24 (1), Avicel® (90 g), sodium carboxymethylcellulose (Ac-Di-Sol; FMC-Asahi Kasei Kogyo Co., Japan) (10 g) and magnesium stearate (0.6 g) were mixed and tableted with a pounder (plain) of 10 mm in diameter at 0.2 ton/cm² to obtain tablets.

The dissolution rates of caffeine from the fine granules obtained in Example 24 and the tablets obtained in Example 25 are shown in Table 11.

TABLE 11

| | Dissolution (%) | | | | | |
|---|---|---|---|---|---|---|
| | Hour | | | | | |
| | 1 | 2 | 3 | 4 | 5 | 6 |
| Fine granules | 16.1 | 24.5 | 33.4 | 38.3 | 43.8 | 46.5 |
| Tablets from coated fine granules | 17.2 | 27.8 | 36.7 | 45.5 | 48.9 | 51.4 |

As seen from Table 11, caffeine release from the tablets produced by tabletting coated fine granules (Example 25) occurs in the same rate as from the coated fine granules not being compressed to tablets (Example 24), and the both preparations exhibit stable release-controlling ability.

EXAMPLE 26

PS-310 (64 g) and MS-310 (16 g) were melted together by heating at 90° C., and 20 g of delapril was thrown thereinto and dispersed by stirring for 30 minutes maintaining the mixture at 70° C., followed by treating in the same manner as Example 1 to obtain 60/80 mesh of spherical fine granules. The dissolution rates of delapril from the fine granules are shown in Table 13.

TABLE 13

| | Dissolution (%) | | | | | |
|---|---|---|---|---|---|---|
| | Hour | | | | | |
| | 1 | 2 | 3 | 4 | 5 | 6 |
| 60/80 mesh fine granules | 48.3 | 74.1 | 85.5 | 90.1 | 92.3 | 93.0 |

The fine granules obtained in the above procedure were administered to a rat under fast overnight in a dose of 20 mg/Kg as delapril and the concentration of (N-[N-[(S)-1-carboxy-3-phenylpropyl]-L-alanyl]-N-indan-2-yl) glycine (metabolite of derapuryl hydrochloride) in the blood was determined and shown in Table 14. As a contrast, a solution of depnrayl hydrochloride (4 mg/ml) in 5 W/V % aqueous suspension of gum arabic was used.

TABLE 14

| | Concentration in blood (μg/ml) | | | | | | | |
|---|---|---|---|---|---|---|---|---|
| | Hour | | | | | | | |
| | 0.25 | 0.5 | 1 | 1.5 | 2 | 3 | 5 | 7 |
| 60/80 mesh fine granules | 0.881 | 0.816 | 0.785 | 0.647 | 1.07 | 0.387 | 0.115 | 0.052 |
| Suspension of delapril hydrochloride in 5 w/v % aqueous gum arabic | 5.46 | 4.63 | 0.875 | 0.427 | 0.221 | 0.200 | 0.090 | 0.007 |

As seen from Table 14, in the case of administering the solution of delapril hydrochloride, rapid disappearance of concentration in the blood is observed, but the present fine granules exhibit sustained concentration in the blood corresponding to the dissolution rate. See Table 13 for the dissolution rates of the 60/80 mesh fine granules.

EXAMPLE 27

MS-310 (8 g), PS-310 (32 g) and stearyl tri(mono)glyceride (TS-310; produced by Sakamoto Yakuhin Co., Japan) (40 g) were melted together by heating and the temperature of the mixture was adjusted to 70° C., and then 20 g of delapril was thrown thereinto and dispersed by stirring for 30 minutes, followed by treating in the same manner as Example 1 to obtain 42/60 mesh of fine granules.

EXAMPLE 28

The fine granules (250 g) obtained in Example 27 were loaded into a fluid-bed drier (FD-35; Fuji Sangyo Co., Japan) and sprayed with 5 W/W % solution of hydroxypropylcellulose in ethanol for coating, controlling the inhalant air at 45° C. and granules at 35° C.; thereby coated fine granules were obtained.

EXAMPLE 29

The coated fine granules (100 g) obtained in Example 28, Avicel® (90 g), sodium carboxymethylcellulose (Ac-Di-Sol; FMC-Asahi Kasei Kogyo Co., Japan) (10 g) and magnesium stearate (0.6 g) were mixed and tabletted with a punch (plain) of 10 mm in diameter at the pressure of 0.2 ton/cm² to obtain tablets.

The dissolution rates of derapuryl hydrochloride from the fine granules, coated granules or tablets of Examples 27, 28 and 29 are shown in Table 15.

TABLE 15

| | Dissolution (%) | | | | | |
|---|---|---|---|---|---|---|
| | Hour | | | | | |
| | 1 | 2 | 3 | 4 | 5 | 6 |
| Example 27 | 56.9 | 83.3 | 89.8 | 89.9 | 89.2 | :9&.6 |
| Example 28 | 51.5 | 78.4 | 89.2 | 92.6 | 93.1 | 92.5 |
| Example 29 | 62.9 | 85.9 | 89.5 | 91.0 | 91.9 | 92.5 |

As seen from Table 15, the release of delapril hydrochloride from the present coated fine granules (Example 28) or tablets obtained by tabletting the coated fine granules (Example 29) is unchanged as compared with the fine granules before coating (Example 27), and all of them exhibit stable and sustained dissolution.

EXAMPLE 30

PS-310 (65.6 g) and MS-310 (9.4 g) were melted together at 90° C., and delapril hydrochloride (25 g) was thrown thereinto and dispersed by stirring for 30 minutes maintaining the mixture at 70° C., followed by treating in the same manner as Example 1 to obtain 42/60 mesh of spherical fine granules.

The release of delapril hydrochloride from the fine granules when they were stored at 40° C. is shown in Table 16.

TABLE 16

| | Dissolution (%) | | | | | |
|---|---|---|---|---|---|---|
| | Hour | | | | | |
| | 1 | 2 | 3 | 4 | 5 | 6 |
| Immediately after production | 38.4 | 57.1 | 74.3 | 83.2 | 85.7 | 86.8 |
| After 10 days at 40° C. | 38.9 | 58.8 | 73.2 | 80.7 | 83.8 | 84.1 |
| After 3.5 months at 40° C. | 35.8 | 53.2 | 66.2 | 74.5 | 79.0 | 81.7 |

As seen form Table 16, present fine granules have excellent release-controlling ability even after a long period of storage, which proves that they are extremely stable controlled release preparation.

EXAMPLE 31

The fine granules obtained in Example 17 were filled into capsule No. 1 of J.P. 11 Ed. to obtain a capsule preparation.

EXAMPLE 32

The fine granules obtained in Example 18 were tabletted with a punch (plain) of 6 mm in diameter at the pressure of 0.1 ton/cm² to obtain tablets.

EXAMPLE 33

In the same manner as Example 24 (1) with a 900 rpm rotation number of the disk, employing PS-310 (800 g), MS-310 (100 g) and caffeine (100 g), 12/48 mesh of granules were obtained.

We claim:

1. Fine granules or granules which comprise a pharmaceutically active ingredient dispersed into a matrix which is solid at ambient temperature and and contains a fatty acid ester of a polyglycerol, the ester being present throughout the fine granules or granules; wherein said fine granules are composed of not less than 75 weight % of particles of 500 to 10 µm, not more than 5 weight % of particles of not less than 500 µm, and not more than 10 weight % of particles of not more than 10 µm; and wherein said granules are composed of not less than 90 weight % of particles of 1410 to 500 µm and not more than 5 weight % of particles of not more than 177 µm.

2. Fine granules or granules according to claim 1, wherein microcrystalline wax is contained in the matrix.

3. Fine granules or granules according to claim 2, wherein the fine granules or granules are coated with a coating agent.

4. Fine granules or granules according to claim 1, wherein the fine granules or granules are coated with a coating agent.

5. Fine granules or granules according to claim 1, wherein the amount of the fatty acid ester of polyglycerol in the matrix is about 0.0001 to 50 times the weight of the pharmaceutically active ingredient.

6. A capsule comprising fine granules or granules which comprise a pharmaceutically active ingredient dispersed into a matrix which is solid at ambient temperatures and contains a fatty acid ester of a polyglycerol, the ester being present throughout the fine granules or granules, said fine granules being composed of not less than 75 weight % of particles of 500 to 10 µm, not more than 5 weight % of particles of not less than 500 µm and not more than 10 weight % of particles of not more than 10 µm and said granules being composed of not less than 90 weight % of particles of 1410 to 500 µm and not more than 5 weight % of particles of not more than 177 µm.

7. A capsule comprising fine granules or granules which comprise a pharmaceutically active ingredient dispersed into a matrix which is solid at ambient temperatures and contains a fatty acid ester of a polyglycerol, the ester being present throughout the fine granules or granules, said fine granules being composed of not less than 75 weight % of particles of 50 to 10 µm, not more than 5 weight % of particles of not less than 500 µm and not more than 10 weight % of particles of not more than 10 µm and said granules being composed of not less than 90 weight % of particles of 1410 to 500 µm and not more than 5 weight % of particles of not more than 177 µm, wherein the fine granules or granules are coated with a coating agent.

* * * * *